United States Patent
Warburton et al.

(10) Patent No.: US 7,462,267 B2
(45) Date of Patent: Dec. 9, 2008

(54) REFERENCE ELECTRODE

(76) Inventors: P. Richard Warburton, 1619 Ridge Rd., Moon Township, PA (US) 15108; Mehrooz Zamanzadeh, 1411 Grandview, Apt. 510, Pittsburgh, PA (US) 15211

( * ) Notice: Subject to any disclaimer, the term of this patent is extended or adjusted under 35 U.S.C. 154(b) by 890 days.

(21) Appl. No.: 10/851,129

(22) Filed: May 24, 2004

(65) Prior Publication Data
US 2005/0258039 A1    Nov. 24, 2005

(51) Int. Cl.
*G01N 27/30* (2006.01)
(52) U.S. Cl. .................... 204/435; 204/414
(58) Field of Classification Search ............ 204/414, 204/416, 433, 435
See application file for complete search history.

(56) References Cited

U.S. PATENT DOCUMENTS

| | | | | |
|---|---|---|---|---|
| 3,671,414 A | * | 6/1972 | Grubb | 204/414 |
| 4,053,381 A | * | 10/1977 | Hamblen et al. | 204/416 |
| 5,271,820 A | * | 12/1993 | Kinlen et al. | 204/418 |
| 5,419,826 A | * | 5/1995 | Zirino | 204/416 |
| 6,432,296 B1 | * | 8/2002 | Daniel et al. | 205/789 |

OTHER PUBLICATIONS

McCormick et al, "Polymers, Water Soluble", pp. 464-472 from Kirk-Othmer Encyclopedia of Chemical Technology, Mar. 2006.*

* cited by examiner

*Primary Examiner*—Kaj K Olsen
(74) *Attorney, Agent, or Firm*—P. Richard Warburton

(57) ABSTRACT

A reference electrode consisting of a metal in contact in contact with an electrolyte containing an anion or cation whose concentration in part determines the redox potential of the electrode? This electrolyte contains a polyelectrolyte that partially and reversibly binds this chemical cation or anion thus lowering the free concentration of the cation or anion compared to the osmotic pressure of the same concentration of cation or anion if present as a simple salt. The polyelectrolyte can be anionic or cationic depending on the chemistry of the redox electrode and a thickener may also be added to the electrolyte.

9 Claims, 3 Drawing Sheets

REFERENCE ELECTRODE

FIELD OF THE INVENTION

The filed of this invention is electrochemical reference electrodes and more specifically a method for improving the life time of reference electrodes especially when used in low ionic strength solutions.

BACKGROUND TO THE INVENTION

Reference electrodes are widely used in many different types of electrochemical experiments including measurements with pH electrodes, ion selective electrodes and cathodic protection instrumentation to access and control the corrosion rate of metallic structures. The role of the reference electrode is to provide a stable potential against which other potentials are measured or controlled. A reference electrode typically consists of at least three components 1) a half cell electrode involving a redox couple, and commonly these are of the metal/metal ion type (e.g. silver/silver chloride or copper/copper sulfate) 2) an electrolyte (e.g. 4 M potassium chloride for the Ag/AgCl or saturated copper sulfate solution for the copper/copper sulfate electrode). 3) a junction that separates the internal solution from the external solution being measured. In, for example, the silver/silver chloride reference electrode, a silver wire is coated with a thin layer of silver chloride and the wire is immersed in a solution of saturated potassium chloride (~4 M). For the discussion below the silver/silver chloride reference electrode will be used since it is one of the most commonly used reference electrodes, but the discussions apply to other types of metal/metal ion reference electrodes as well.

The potential E of the electrode s governed by the Nernst equation:

$$E = E° + (RT/nF)\ln\{[ox]/[red]\}$$

where $E°$ is the standard potential, R is the gas constant, T is the temperature, n is the number of electrons, F is the Faraday constant, [ox] is the concentration of the oxidized form of the redox couple and [red] is the reduced form of the redox couple. The electrode reactions for the silver/silver chloride reference electrode are:

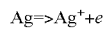

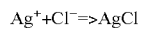

On including these equilibria, the Nernst equation becomes $$E = E° + (RT/nF)\ln\{[AgCl]/(K[Ag][Cl^-]\}$$

where $K=[AgCl]/(Ag^+][Cl^-]$, in which K is the solubility product for silver chloride.

The internal solution must be in ionic contact with the external solution in order for the electrode to function. If the ionic contact is too small, the impedance will be too high and the potential measurement with the reference electrode will be noisy and subject to drift. Therefore a good ionic contact is preferable. However, this ionic contact also allows transport of ions between the internal and external solutions. Contamination of the external solution can be a problem if the measurement is sensitive to, for example, chloride ions leaking from a silver/silver chloride reference electrode. Similarly heavy ions, such as mercurous ions from a calomel reference element, can be a problematic when measuring certain biological media.

Furthermore, unless the external solution has a high chloride concentration (e.g. seawater), there will be a steady loss of chloride from the reference electrode internal solution to the external solution since there is a concentration gradient and diffusion of the external solution into the reference electrode potentially causing contamination of the reference electrode and possible variation in the electrical potential. In order to keep the potential constant, the potassium chloride concentration must be kept constant, which is normally done by using a saturated solution. The internal chloride concentration and hence the electrode potential will be kept constant by the dissolution of any solid potassium chloride present, but once that has all dissolved, the internal chloride concentration will decrease and the potential of the electrode will change accordingly as described by the Nernst equation (vide supra).

Several methods have been employed in the prior art to mitigate this problem. The traditional method used to prevent mixing of the inner solution of the reference electrode with the test solution was to separate the two by a salt bridge. The salt bridge was typically a tube filled with a gelled solution of another salt (e.g. potassium nitrate) that would not interfere with either the test solution or the reference electrode, but the salt solution provided the ionic contact necessary for the function of the reference electrode; however this approach tends to be cumbersome.

Another common way to avoid the problem of loss of chloride is to add a reservoir of saturated potassium chloride and is to make the reference electrode inner chamber refillable. When the internal chloride solution decreases or the electrolyte dries out, the user simply adds more saturated potassium chloride solution. Many commercial reference electrodes are refillable. Thus potassium chloride solution is constantly flowing out of the reference electrode. This configuration works well for some applications, but is unsuitable for situations where the external solution should be kept free of chloride ion, or where the reference electrode is to be left in place for a long period of time without maintenance. For example, reference electrodes for cathodic protection systems to prevent the corrosion of underground steel pipes may only be serviced every six months or more.

Another method that has been extensively utilized is to provide a barrier between the inner solution and the external solution. If the barrier characteristics are chosen correctly, then the ionic contract is sufficient to achieve good performance from the reference electrode, yet the rate of chloride ion transport out of the reference electrode is slow enough that the reference electrode can be used in a wide variety of applications.

In most reference electrodes, the sample electrolytes make contact to the inner solution either by slow flow of salt bridge solution through the barrier into the sample, called a flowing junction electrode, or by mutual diffusion into the porous structure from each side, called a static junction electrode. Typical barriers include ceramic and glass sinters and capillaries, ground glass sleeves, wooden plugs (Cardiero, U.S. Pat. No. 3,440,525) glass—plastics composites (e.g. Neti and Bing, U.S. Pat. No. 4,002,547) and Teflon powder treated to make its surface hydrophilic (Maruyama and Watanabe, U.S. Pat. No. 4,053,382) and more recently microfluidic flowing junctions (Broadley et al, U.S. Pat. Nos. 6,599,409 & 6,616, 821) and ion conductive membranes (Connelly and Bower U.S. Pat. No. 6,579,440). Liquid junctions, utilizing ion conductive membranes have also been used (e.g. by Spaziani and Fowler, in U.S. Pat. No. 4,233,136 and Leonard in U.S. Pat. No. 4,913,793). Ion exchange polymers, both water soluble and in-soluble types, have been used as junctions in reference electrodes resulting in good performance in low osmotic pressure solutions Leonard U.S. Pat. No. 4,913,793.

To further reduce the ingress and egress of the external and internal solutions respectively one common approach is to have more than one junction, and so called 'double junction' reference electrodes are now widely used. (e.g. Watanabe and Leonard in U.S. Pat. No. 3,103,480, Arrance, in U.S. Pat. No. 4,282,081, Brezinski, U.S. Pat. No. 4,401,548). In addition to loss of electrolyte and contamination another common failure mode is blockage of the junction. Replaceable junctions (e.g. Brezinski, U.S. Pat. No. 4,495,052) are one common method that is employed to overcome clogging of the liquid junction (see below).

Another common method used to reduce the loss of chloride from the reference electrode is to incorporate a gelling agent into the reference electrolyte. The gelling agent reduces the diffusion rate of all species present and so extends the lifetime of the reference electrode. However, as with the other methods that extent the lifetime of the reference electrode by reducing the diffusion rate, a balance is required between the diffusion rate and electrical noise resulting from high impedance if the diffusion rate is too small. There are many examples of gelling agents used including gelatin, agar, sodium carboxymethylcellulose, polyacrylamides, and more recently hydrogels (Thrier et al U.S. Pat. No. 6,468,408). Reference electrodes have also been made with electrolytes solidified with various hydraulically setting cements (Tauber and Dornauf, U.S. Pat. No. 4,927,518).

There are several failure modes of reference electrodes related to the loss of electrolyte by diffusion. The first method is as outlined above, involves direct loss of the electrolyte by diffusion. However, diffusion is not the only mechanism that leads to the loss of electrolyte. If the reference electrode is used in a low ionic strength solution and the internal solution is a high ionic strength solution (e.g. saturated potassium chloride), then the osmotic pressure is going to act to push the low ionic strength external solution into the reference electrode. Since the reference electrode chamber is usually sealed apart from the diffusion barrier (e.g. sinter), the net effect is that the osmotic pressure flushes the electrolyte out of the reference electrode chamber causing a shortened lifetime. Temperature changes can cause pressure imbalances between the inside of the reference electrode chamber and the external environment. These pressure changes can lead to additional mass flow across the barrier.

Another common method by which silver/silver chloride electrodes fail is blockage of the sinter by silver chloride. Silver chloride (AgCl), though insoluble in water, has some solubility in high concentrations of chloride ion through the reversible formation of the $AgCl_2^-$ complex and higher chloride ion complexes. If the reference electrode is used in a low chloride test solution, then the soluble silver chloride will revert back to the insoluble silver chloride where the internal and external solutions meet, i.e. in the barrier, resulting in blockage of the barrier and failure of the reference electrode. Blockage of the sinter can occur rapidly, for example Brezinski in U.S. Pat. No. 4,401,548 reports that a new silver/silver chloride reference electrode can lose most of its flow capability after less than 24 hours in solution.

Metal ions in the external solution that form insoluble salts with chloride ion (typically the heavy metals: silver, lead, and mercury) can also precipitate in the liquid junction leading to failure of the reference electrode. Of course contamination can simply block the barrier causing the reference electrode to fail even without specific chemical reaction.

Contamination of reference electrodes, especially by compounds that form insoluble species on mixing with the redox active metal salt is another common cause of failure, for example, sulfide containing test solutions can adversely affect silver/silver chloride and calomel reference electrodes through the precipitation of silver sulfide compounds in the barrier.

The primary driving force for many of these failure mechanisms is the high electrolyte concentration required in the reference electrode electrolyte (e.g. 4 M KCl). This high concentration of electrolyte especially limits the use of reference electrodes in low ionic strength solutions (e.g. in fresh water) and for long term applications, such as corrosion monitoring. A method is needed that will allow a reference electrode to be used in low ionic strength solutions, that can be combined with conventional barriers and conventional electrolyte gelling methods and which utilizes conventional redox chemistry but which can extent the lifetime of the reference electrode by employing a low internal ionic strength electrolyte.

SUMMARY OF THE INVENTION

The present invention consists of a conventional reference electrode, such as a silver/silver chloride reference electrode, using a polyelectrolyte solution as the electrolyte instead of a conventional salt electrolyte.

An object of this invention is to provide a reference electrode that has extended service life in low ionic strength solutions A further object of this invention is to provide a silver/silver chloride reference electrode that is resistant to failure in low ionic strength solutions by precipitation of solid silver chloride in the diffusion barrier.

A still further object of this invention is to provide a reference electrode electrolyte than can be readily and controllable gelled by addition of conventional gelling agents, barriers and other components of reference electrodes.

DETAILED DESCRIPTION OF THE INVENTION

Figure 1:
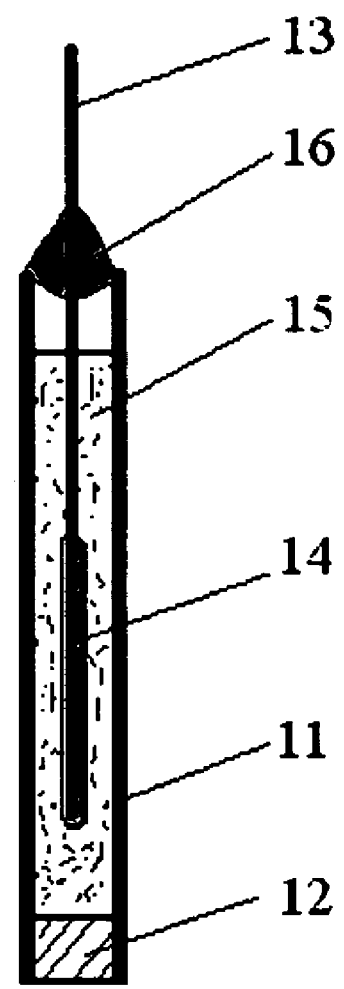
FIG. 1 A conventional silver/silver chloride reference electrode

The first embodiment of this invention is illustrated by a silver/silver chloride reference electrode, shown in FIG. 1. The reference electrode 10 consists of a chamber 11 that may be made of glass, plastic (e.g. polycarbonate), or any other material that is conventionally used for this application, both rigid and flexible such as polyolefin tubing (Grubb, U.S. Pat. No. 3,705,089). The chamber 11 is closed at one end with a barrier 12. The barrier 12 is preferably a ion permeable barrier such as porous ceramic sinter but any other type of barrier conventionally used in a reference electrode may also be used. A silver wire 13 coated with silver chloride 14 is inserted into the chamber. The silver wire 13 is coated with silver chloride 14 by conventional means, for example electrolysis in potassium chloride solution. The Chamber is also filled with an electrolyte mixture 15. The electrolyte 15 mixture consists of an aqueous solution of a polyelectrolyte in the chloride form. Examples of suitable polyelectrolytes are poly (diallyldimethyl ammonium chloride) and poly(vinylbenzyltrimethylammonium chloride). These compounds are intended to provide illustrative examples of suitable polyelectrolytes, however other polyelectrolytes may readily be used as alternatives or in addition to the two examples herein. Polyelectrolytes are a well known field of chemistry, as is illustrated by the following text books {A. Rembaum, E. Selegny, "Polyelectrolytes and their Applications, (1975), D. Reidel Pub. Co., Dordrect, Holland; F. Oosawa, "Polyelectrolytes", (1971), Marcel Deckker Inc. New York, N.Y. The means for identification of other polyelectrolytes is well known to those skilled in the art of chemistry in light of the present disclosure. The optimum concentration of the polyelectrolyte will vary with the solubility of the polyelectrolyte in water and with the other physical properties of the solution and is best determined experimentally and if desired combinations of polyelectrolytes can also be used. For example, a concentration of the above polyelectrolytes between 5 and 95% is preferred with a most preferred concentration around 10 to 30% by weight polymer in the solution. The cell shown in FIG. 1 is generally similar to other cells used for reference electrodes in the prior art and many variations on the cell design are possible as is well known in the art of electrochemical science.

The electrolyte 15 is preferably water based, however if the sample solution in which the reference electrode is to be used is non-aqueous, then it may be desirable to use a non-aqueous or mixed aqueous/non aqueous electrolyte in combination with the polyelectrolyte. Provided that the solvent system used allows the physical objectives of using the polyelectrolyte in a reference electrode as is described herein, other solvents systems can be used to formulate the electrolyte 15 within the scope of this invention.

The electrolyte 15 can also contain gelling agents to increase the viscosity of the electrolyte 15. Increasing the viscosity can both reduce the diffusion rate and so extend the lifetime of the reference electrode 10, and it can also prevent the electrolyte 15 from moving inside the reference electrode 10. Many gelling agents are available for increasing the viscosity of the electrolyte 15. For saturated potassium or sodium chloride solutions, many gelling agents (e.g. gelatin) do not increase the viscosity of the solution since the high ionic strength prevents the gelling process or greatly reduces the efficiency of the gelling process. However with the polyelectrolytes, the ionic strength is much lower and so the efficiency of gelling process is improved and so the choice of gelling agents is broader. Suitable gelling agents include agar, gelatin, polyacrylic resins, hydroxylethylcellulose and polyethylene oxide. Most thickeners and gelling agents intended for aqueous solution can be used.

Typical concentrations of, for example, hydroxylethylcellulose, in the above exemplary polyelectrolytes solutions between 1 to 5% w/w provide a solution with good thickening and gelling properties. However, this value is intended to be illustrative only since the concentration of the thickening/gelling agent will depend upon the type and grade of gelling/thickening agent used, the type and concentration polyelectrolyte used and other components in the electrolyte. Therefore the optimum concentration of the gelling/thickening agents is best determined experimentally. Other gelling agents and concentrations can be used instead or in addition to the ones listed and the means for their selection is well known to those skilled in the art of chemical formulation and as is used in conventional reference electrodes with gelled electrolytes.

If a non-aqueous solution or mixed aqueous/non-aqueous solvent system is used in the reference electrode, then a gelling agent suitable for that solvent system should be used.

The polyelectrolyte are large polymers and in contrast to the saturated salt solution electrolyte, they typically either do not affect or symbiotically affect the gelling agent since the latter is also usually a large water soluble polymer. Thus forming the gelled electrolyte often requires less of the gelling agent than for a saturated salt electrolyte to achieve the same viscosity.

The top 16 of the reference electrode 10 is sealed by conventional means, for example silicone sealant, epoxy resin etc. If desirable, a fill hole with cover (not shown) can be included at the top of the reference electrode 10 to allow easy filling of the electrode.

The use of the polyelectrolyte provides several advantages to the reference electrode compared to traditional saturated salt electrolytes. Even though the chloride content of the electrolyte is high, much of the chloride is bound to the polyelectrolyte. Therefore the ionic strength of the solution is low. This feature provides low ionic strength of the electrolyte that provides the beneficial properties of this invention, but the high bound chloride concentration provides a long term reservoir of chloride ion that allows for long reference electrode life.

The lower free chloride concentration in the electrolyte 15 results in a lower rate of diffusion of chloride ion out through the diffusion barrier 12 in applications where the external solution has a low chloride concentration since the rate of diffusion depends on the concentration gradient. This lower rate of chloride diffusion reduces contamination of the external test solution and extends the lifetime of the reference electrode 10.

The effective molecular weight of the chloride is not that of the chloride alone, but also is depends on the molecular weight of the polymer, otherwise there would be an imbalance of charge if the chloride anions diffused separately from the cationic polymer. Therefore the diffusion rate of the chloride ions is lower than would be for the same concentration of a simple salt such as sodium chloride. The lower rate of diffusion of chloride ion again tends to extend the lifetime of the reference electrode 10.

The use of an electrolyte containing ions of different diffusivities is often avoided in traditional reference electrode design, where the ions are selected to be equitransferent in order to allow for very fast response times and low junction potentials. However, for many applications, a very fast response time is of less importance than the long life achievable with the polyelectrolyte electrolytes and the lower chloride concentration will result in the polyelectrolyte reference electrodes having slightly different potentials from the text book values of the redox couples (e.g. Silver/silver chloride), but this difference in potential is easily accommodated in most applications.

The lower ionic strength of the polyelectrolyte electrolyte mixture results in a lower osmotic pressure difference between the internal and external solutions and therefore the rate of osmotic pressure flushing of the electrolyte as is also greatly reduced compared to the rate that can occur with conventional saturated salt electrolytes. The lower ionic strength of the polyelectrolyte electrolyte thus allows the reference electrode 10 to have a much longer life than a comparative reference electrode made with a saturated potassium chloride electrolyte, especially in low ionic strength solutions, such as fresh water streams, rivers, swimming pools etc.

The polyelectrolyte method can be applied to other types of reference electrode as well. The above chloride polyelectrolytes can be used with other chloride based reference electrodes, for example the calomel reference electrode, which consists of metallic mercury in contact with calomel ($Hg_2Cl_2$) in contact with saturated potassium or sodium chloride solution. As before, the polyelectrolyte can be used to replace the saturated simple salt electrolyte. Obviously if another anion were to be part of the redox couple, such as the mercury/mercury sulfate reference electrode, then a polyelectrolyte in the form (e.g. sulfate) for that anion could be used.

Conversely, where the electrolyte cation in parts determines the concentration of the reference electrode potential (e.g. Cu/Cu(II)), then a polyelectrolyte with an anionic structure would be required and it would be associated with the appropriate cations. For example, a copper/copper sulfate reference electrode is normally prepared by immersing a copper wire into an electrolyte saturated with copper (II) sulfate.

A polyelectrolyte in the form of the appropriate metal ions can be formed using conventional means by reacting the polyelectrolyte in the acid with a basic salt of the metal. For example, a copper (II) polyelectrolyte can be formed by reacting the acid form of the polyelectrolyte with an approximately stoichiometric amount of a basic copper salt (e.g. oxide, carbonate, bicarbonate). Examples of suitable polyelectrolytes are polysulfonic acid and polyacrylic acid. Many other polyelectrolytes are known and copper or other metal salts of them can be prepared by the above or other standard methods as are well known to those skilled in the art of chemistry. Most other conventional means for producing metal ion compounds can also be employed and the choice of method and the optimum conditions will depend on the properties of the metal and polyelectrolyte polymer chosen and these conditions are readily determined by those people skilled in the chemical arts.

The use of a copper/copper sulfate reference electrode was chosen because copper/copper sulfate is a widely used reference electrode, but it also illustrates that the advantages of using polyelectrolytes in the electrolytes of reference electrodes can be applied to a many different types of reference electrode, including reference electrodes in which the concentration of the cation in the electrolyte solution determines the reference electrode potential and for reference electrodes in which the concentration of the anion in the electrolyte determines the potential of the reference electrode.

This invention can be applied to many applications for reference electrodes. For example, it can be used for stand-alone laboratory type reference electrodes, electrodes for implantation in soil, or biological tissue (provided the polyelectrolyte is selected to be biologically compatible), in combination electrodes (e.g. pH electrodes and ion selective electrodes). While it is preferable to use the polyelectrolyte with the appropriate counter ion in a suitable solvent as the electrolyte, a mixture of polyelectrolytes and/or solvents can also be used. Also, the use of a mixture of the polyelectrolyte with one or more salts is also within the scope of this invention.

EXAMPLE A

Figure 2:
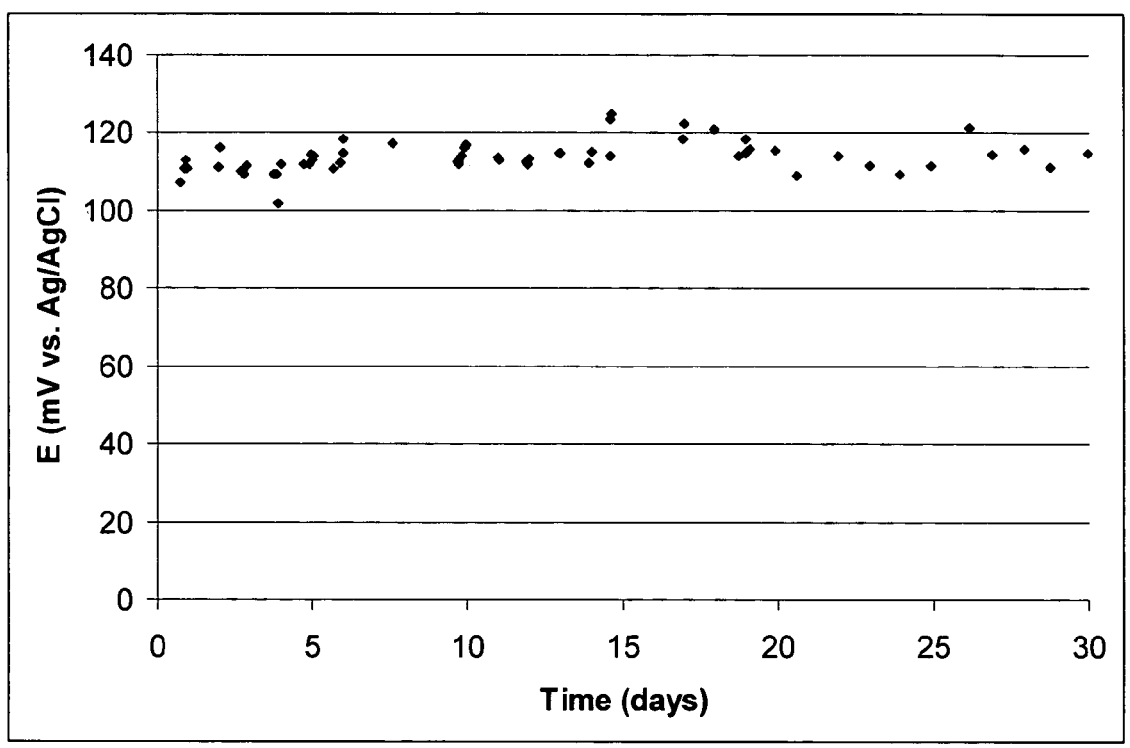
FIG. 2 Lifetimes tests of conventional and polyelectrolyte silver/silver chloride reference electrode semi-immersed in tap water FIG. 3 Lifetimes tests of conventional and polyelectrolyte copper/copper (II) ion reference electrodes semi-immersed in tap water

A silver/silver chloride reference electrode was prepared by coating a silver wire with silver chloride by electrolysis in saturated sodium chloride solution (Voltage ramp, 0 to 0.5 V, 10 mV/s vs. SCE), and inserting into a solution of poly(diallyldimethylammonium chloride) (Sigma-Aldrich Chemical Company, Milwaukee, Wis.) 20% w/w in a 2" long ¼" OD vinyl tube closed at one end with a sintered plastic disk (Porex Corporation), and sealed at the other end by a silicone sealant. Lifetime data for this electrode is shown in FIG. 2. The X-axis is the time from manufacture of the electrode. The electrode was fabricated; left one day for the sealant to set and then the electrode was placed in tap water and left there. There is significant variation with time, however much of this variation comes from the comparison standard reference electrode used to make the measurements as judged by the fact that much of the variation was systematic between test electrodes. However, as can be seen in FIG. 2, there was no systematic variation in output after thirty days in tap water.

EXAMPLE B

Figure 3:
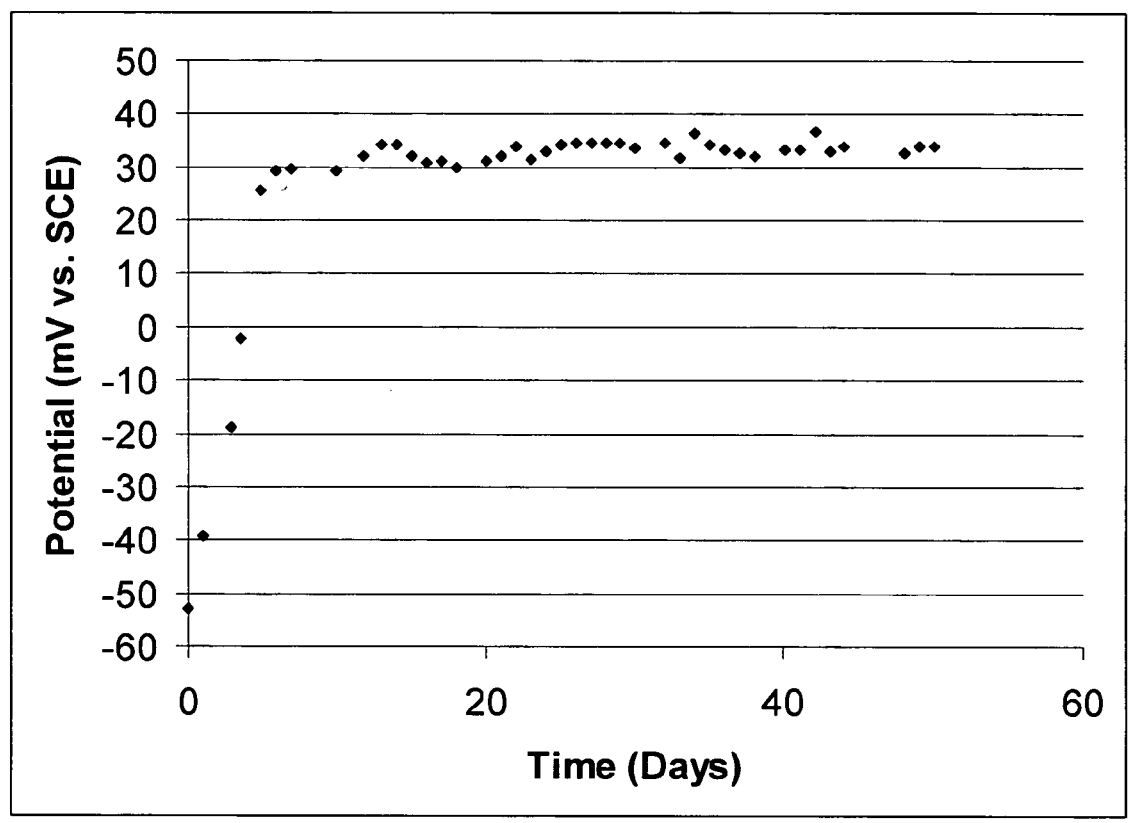

A copper ion based polyelectrolyte reference electrode was be prepared by substituting the saturated copper sulfate solution for copper polysulfonic acid (prepared by reacting polysulfonic acid with stoichiometric amount of copper (II) carbonate). A reference electrode was constructed in similar manner to that described in Example A, except that a copper wire was used instead of the silver chloride coated silver wire and the electrolyte was substituted for the one described herein. This reference electrode was similarly tested. The lifetime data for this sensor in tap water are shown in FIG. 3. This electrode exhibited a much improved lifetime compared to simple copper/copper sulfate reference electrode of similar construction, which failed within a couple of days under similar test circumstances. This electrode required several days for the potential to equilibrate after being left in water, but once it equilibrated the potential remained stable with time. As can be seen from FIG. 3, there was no systematic shift in the potential for over a month of immersion in tap water. Most of the variation from day to day was due to the reference electrode against which the potentials were measured as evidenced by the fact that other electrodes being tested at the same time showed the same variation with time and against the same electrode. The electrolyte volume within this test electrode was small, approximately 0.2 ml, i.e. much smaller than most commercial reference electrodes. As with other types of silver/silver chloride reference electrode, the lifetime is expected to improve with a larger electrode volume.

The following description is provided to enable any person skilled in the art to make and use the invention, and sets forth the best modes contemplated by the inventors in carrying out his invention. Various modifications, however, will remain readily apparent to those skilled in the art, since the generic principles of the present invention have been defined herein specifically to provide an improved and economical reference electrode that resolves recurring problems in the prior art.

We claim:

1. An electrochemical reference electrode comprising of an enclosure, that contains an electrolyte, said enclosure incorporating a barrier for providing ionic contact between the said electrolyte and an external solution, and a metallic electrode within the said enclosure, said metallic electrode in contact with the said electrolyte, means for providing external electrical contact to said metallic electrode, said electrolyte containing an ionic species whose concentration in part determines the redox potential of said electrode and said electrolyte also containing in part a polyelectrolyte that binds at least partially and reversibly binds the ionic species, such that said polyelectrolyte materially affects the potential of the said electrode by controlling the concentration of the free ionic species.

2. The reference electrode as described in claim 1, where the polyelectrolyte contains sulfonic acid or carboxylic acid functional groups.

3. The reference electrodes as described in claim 1, wherein the polyelectrolyte contains a quaternary ammonium functional group.

4. The reference electrode as described in claim 1, wherein the electrolyte consists of the polyelectrolyte as a solution in water.

5. An electrochemical reference electrode comprising of an enclosure, that contains an electrolyte, said enclosure incorporating a barrier for providing ionic contact between the said electrolyte and an external solution, and a silver electrode within the said enclosure, said silver electrode in contact with the said electrolyte, means for providing external electrical contact to said metallic electrode, said electrolyte containing one or more of the following anions, chloride, bromide, and nitrate, whose concentration in part determines the redox potential of said electrode and said electrolyte also containing in part a polyelectrolyte that binds at least partially and reversibly binds the anions, such that said polyelectrolyte materially affects the potential of the said electrode by controlling the concentration of the free ionic species.

6. The reference electrode as described in claim 5, where the polyelectrolyte contains a quaternary ammonium functional group.

7. The reference electrode of claim 5 wherein the silver wire is coated with silver chloride.

8. An electroctlemical reference electrode comprising of an enclosure, that contains an electrolyte, said enclosure incorporating a barrier for providing ionic contact between the said electrolyte and an external solution, and a copper electrode within the said enclosure, said copper electrode in contact with the said electrolyte, means for providing external electrical contact to said metallic electrode, said electrolyte containing a copper (II) ions and said electrolyte also containing in part a polyelectrolyte that binds at least partially and reversibly binds the copper ions, such that said polyelectrolyte materially affects the potential of the said electrode by controlling the concentration of the free ionic species.

9. The reference electrode as described in claim 8, where the polyelectrolyte contains a sulfonic acid or carboxylic acid functional group.

* * * * *